United States Patent
Azizova et al.

(10) Patent No.: US 7,048,770 B2
(45) Date of Patent: May 23, 2006

(54) HAIR COLORING AND CONDITIONING COMPOSITION

(75) Inventors: Mariana Azizova, Rowayton, CT (US); Rushi Tasker, Trumbull, CT (US); Lorraine Takor Oben, Fairfield, CT (US)

(73) Assignee: Zotos International, Darien, CT (US)

( * ) Notice: Subject to any disclaimer, the term of this patent is extended or adjusted under 35 U.S.C. 154(b) by 339 days.

(21) Appl. No.: 10/623,780

(22) Filed: Jul. 21, 2003

(65) Prior Publication Data

US 2005/0015895 A1  Jan. 27, 2005

(51) Int. Cl.
*A61K 7/13* (2006.01)
(52) U.S. Cl. .................. 8/405; 8/406; 8/410; 8/411; 8/421; 8/552; 8/554; 8/555; 8/558
(58) Field of Classification Search .............. 8/405, 8/406, 410, 411, 421, 552, 554, 555, 558
See application file for complete search history.

(56) References Cited

FOREIGN PATENT DOCUMENTS

JP  2000297019 A  * 10/2000

OTHER PUBLICATIONS

Kasugai Masaaki, JP 2000297019 A (English abstract) Oct. 24, 2000.*

* cited by examiner

*Primary Examiner*—Eisa Elhilo
(74) *Attorney, Agent, or Firm*—Melvin I. Stoltz

(57) ABSTRACT

By providing certain quaternary terpolymers as an integral ingredient in hair coloring formulations, substantially improved and enhanced hair conditioning benefits are attained, providing a highly effective, hair coloring composition which also provides conditioning benefits to the hair fibers. In addition, the conditioning benefits and effects are long lasting and capable of being retained by the hair fibers for up to four weeks.

9 Claims, No Drawings

HAIR COLORING AND CONDITIONING COMPOSITION

TECHNICAL FIELD

This invention relates to hair coloring compositions and, more particularly, to hair coloring compositions which also provide conditioning benefits to the hair fibers.

BACKGROUND ART

Throughout the years, there has been a desire to alter the color of synthetic and natural fibers. In particular, coloring of human hair has been sought in view of changing styles and fashion. However, due to the inherent composition of hair fiber, and the chemical and mechanical exposure encountered by the hair fibers during normal care and styling, obtaining and maintaining a precise color has been an illusive goal.

As is well known, hair is composed of a unique protein material called "keratin" which is repeatedly being subjected to both chemical and mechanical damage from combing and brushing, as well as from sunlight, chlorinated water, shampooing, permanent waving, and other such treatments involving various chemicals. As a result, depending upon the length of the hair fibre, the distal ends of each hair fiber tend to have substantially more damage than the proximal ends nearer to the scalp. This inconsistency causes variation in the dye uptake by the hair fiber, resulting in color variations along the length of the hair fiber.

In spite of the long history with the coloration of hair and the extensive effort that has been expended in attempting to eliminate the problems associated with the dyeing of human hair, no system has been achieved which is capable of overcoming all of the drawbacks and difficulties encountered with hair dyes. Included among these drawbacks is the need for a dye system which avoids any adverse effect on the skin or hair of the user.

Other problems which continue to plague conventional prior art dyes are the longevity or wearability of the resulting color, its ability to resist fading, and its ability to resist changes due to washing, combing, or rubbing. Furthermore, the accuracy of the color imparted to the hair fiber during the dyeing process, as well as the ease with which the hair fiber is capable of being dyes, are also important factors which prior art dye compositions have been incapable of successfully overcoming.

In general, prior art hair coloring and fiber coloring mixtures comprise dyestuffs obtained from coal tar derivatives or from synthetic routes. These mixtures are typically formulated to provide a particularly desired wearability of the color on the fiber. Dyes formulated for coloring hair fibers, are typically termed temporary, semi-permanent, or permanent.

Temporary dyes or hair colors last through a few shampooings, while semi-permanent hair colors are retained for three to six weeks of shampooings. The permanent dyes or colors, which are often equally employable on plant derived and synthetic fibers, as well as hair keratin, cannot be shampooed out from hair fibers.

It is well known that many standard colors employed on hair or on synthetic fibers cause irritation due to the sensitivity of many individuals to these dyes. As a result, in the case of human application where hair is being dyed, a pre-application is required. In this pre-application, a small amount of color mixture is applied to the skin of the individual and allowed to remain thereon for a period of twenty-four hours, prior to use, in order to assure that an adverse reaction will not occur. If an adverse reaction is found, the dye formulation cannot be used.

It has also been found that repeated contact of the human skin to many prior art dye formulations derived from coal tars and synthetic routes often results in discomfort to the individual receiving the dye application. In addition, various other disadvantages are often encountered with the use and application of standard dyes and their application procedures.

Non-permanent dye formulations are principally employed in the coloring of human hair. Furthermore, most compositions used for temporarily tinting hair fibers contain acid dyes.

The nature of these non-permanent dyestuffs is to coat the fiber where the dyestuff remains on the surface of the fiber, due principally through weak electrostatic interaction. As a result, any mild mechanical stress, such as is caused by rubbing or combing the hair, causes much of the dyestuff to be removed. Furthermore, shampooing or immersion of the hair into water for any protracted time period results in a complete removal of the dyestuff and, hence, the temporary nature of the resulting color.

Semi-permanent hair coloring compositions typically comprise mixtures of one or several dyestuffs in a solution containing alcohol and water. Often the hair coloring is employed in a foam base which allows the product to be applied in various "shampoo-in" applications.

The amount of color deposited on the hair by such applications is subject to substantial variations, although the actual color deposited is typically low. In addition, grey hair is the most difficult to color in this way and loses the applied color most rapidly upon shampooing. As a result, repeated re-applications are necessary.

If an individual does not regularly have the color reapplied, the hair fibers will develop an uneven hair color, due to an uneven distribution of the dye along the hair fibers. This produces an unnatural appearance and cast to the hair. Furthermore, the repeated use required by such product causes the excess dyestuff rinsed from the hair to enter the waterways, thereby adding to the cumulative problems presently being realized in the contamination of ground water.

In view of the difficulties and drawbacks detailed above in regard to semi-permanent hair colors and temporary hair colors, individuals wishing to dye their hair have sought the use of permanent dye formulations. In particular, professional hair stylists prefer the use of permanent dye formulations, since they wish to provide their customers with more durable and longer lasting results.

In using virtually all prior art permanent hair dyes, hydrogen peroxide is required along with the particular dyestuffs. During the application, the mixture enters into the hair fibers and reacts therein to form larger dyes of a predetermined color. Since the dy molecules formed are larger than the molecules entering the hair fibers, the formed dyes are trapped within the hair fibers, and are unable to diffuse out of the fibers. Consequently, the resulting coloring is trapped within the hair fiber and is permanent.

One advantage that has been found from using these types of dye mixtures is the ability to lighten hair, since the presence of both hydrogen peroxide and the alkaline environment of the mixture will also remove natural hair color, which is then replaced by the colors formed in situ. Unfortunately, many of the dye precursors used in the formation of permanent hair colors are known to be sensitive to many individuals and, in some cases, have purported to be active in biological systems in causing interference with different aspects of cellular action.

In addition, another principal concern that has existed in the prior art is that the typical processes used to color hair involve contacting the hair with a mixture of dyes and ammonia and hydrogen peroxide. This combination can cause irreversible damage to the keratin matrix of the hair fiber. Furthermore, in order to be effective, the process requires some mode of swelling of the hair to allow for the penetration of the dye. In the case of tint impartation, whereby the deposited color is a shade or tone lighter than the naturally underlying color, a bleaching of the natural color is required.

Due to the attention that has been given to hair dyeing, the mechanisms involved in the action of the dye formation are well understood. In addition, the damage done to the hair fibers is also well-known. In particular, some characteristics of this damage are the dimmunization of the structural integrity of the hair fibers, as evidenced by the loss of resiliency and increased porosity or capability to uptake water.

As is apparent from the preceding discussion, numerous attempts and extensive effort has been expended through the long history of dye use to achieve a commercially successful dye product. However, no such product has been attained which is capable of providing a universally applicable, commercially acceptable product which overcomes all of the known drawbacks. In addition, the prior art dye systems have often proven to be expensive, while providing only limited or partial success.

Therefore, it is a principal object of the present invention to provide a permanent or long lasting dye composition for use on human hair which is non-toxic and capable of being easily and successfully employed on all desired hair fibers with consistent, repeatable and predictable coloration results, while also imparting a long lasting conditioning effect on the hair fibers.

Another object of the present invention is to provide a permanent dye composition having the characteristic features described above which is long lasting, durable and incapable of being washed from the fibers.

Other and more specific objects will in part be obvious and will in part appear hereinafter.

DETAILED DESCRIPTION

By employing the present invention, the prior art failings and drawbacks have essentially been overcome, and a highly effective, hair coloring compositions is obtained which also provides conditioning benefits to the hair fibers. Typically, the conditioning benefits and effects are long lasting, capable of being retained by the hair fibers for up to four weeks.

In accordance with the present invention, it has been found that certain quaternary terpolymers can be used as conditioners in hair coloring formulations. By employing these quaternary terpolymers in the hair coloring formulations, substantially improved and enhanced hair conditioning benefits are attained.

It is believed that the quaternary terpolymers deposit themselves on the hair fibers and form a bond with the negatively charged surface of the hair. In addition, it has been found that the polymers remain on the hair fibers for a longer period of time, even after numerous washings with anionic shampoos. The deposition of the polymers on the hair fibers can be temporary or long lasting, depending upon the structure of the polymer being employed in the hair coloring treatment.

Frequently, hair coloring compositions are formulated at a pH ranging between about 9.5 and 10.5. Hair coloring compositions formulated at this pH level often affects the integrity of the hair fiber, by swelling the cuticle layer of the hair fiber. However, this swelling allows the polymer of the present invention to partially penetrate directly into the hair fiber. In this way, the polymers of the present invention are capable of achieving a longer lasting effect and are particularly suited for such hair coloring compositions.

The particular polymers that have been found to be effective in imparting a strong cationic moiety on the hair fibers, while also providing conditioning to the hair fibers are amphoteric terpolymers consisting of repeating units of (1) polyacrylic acid, (2) a cationic monomer, such as one selected from the group consisting of dimethyidiallyl ammonium chloride (DMDAAC) and methacrylamidopropyl trimethyl ammonium chloride (MAPTAC), and (3) a non-ionic monomer. Non-ionic monomers useful in the present invention which may be used to prepare the quaternary terpolymer of this invention are preferably non-ionic derivatives of acrylic acid. The preferred non-ionic monomer is acrylamide.

In the present invention, the preferred amphoteric terpolymer comprises Polyquaternium 53 (Merquat 2003), which is distributed by Nalco Chemical Co. of Naperville, Ill. In this preferred terpolymer, the ratio of the cationic moiety (MAPTAC or DMDAAC) to the anionic moiety (acrylic acid) is preferably 4:1. Additionally, all or most of the acrylic acid is neutralized during the polymerization process to become sodium methacrylate.

As detailed herein, the present invention is directed to a hair dye or hair coloring composition comprising a mixture of oxidative dyes and/or direct dyes in combination with a quaternary terpolymer comprising repeating units of (1) methacrylamidopropyl trimethyl (MAPTAC), (2) the acrylic acid and/or sodium methacrylate, and (3) acrylamide, with the ratio of (1) to (2) being 4:1 or higher. In addition, the composition of the present invention may be mixed with a developer containing at least one oxidizing agent selected from the group consisting of peroxide, perborate, percarbonate, and other similar agents.

The hair dye or hair coloring composition of the present invention preferably comprises between about 0% and 5% by weight based upon the weight of the entire composition of the oxidative dye and/or the direct dye, and between about 0% and 5% by weight based upon the weight of the entire composition of the amphoteric terpolymer. In addition, the preferred amphoteric terpolymer comprises a reaction product consisting of about 25 mole percent of acrylic acid and/or sodium acrylate, about 50 mole percent of MAPTAC, and about 25 mole percent of acrylamide.

Furthermore, in formulating the hair dye or hair coloring composition of the present invention the oxidative dye and/or direct dye is preferably selected from the group consisting of p-phenylenediamine, p-tolyenediamine, and its derivatives, N,N-Bis(2-hydroxyethyl)-p-phenylenediamine, p-aminophenol, 2-chloro-p-phenylenediamine, 2-methoxy-p-phenylenediamine, resorcinol, 1-naphthol, 2-amino-3-hydroxytoluene, m-aminophenol, p-amino-o-cresol, 2-methylresorcinol, m-phenylenediamine and mixtures thereof. By combining one more dyes selected from this group with the preferred composition for the amphoteric terpolymer, the desired hair dye or hair coloring composition of the present invention is realized.

In Table I, the overall formulation for the hair dye/hair coloring composition of the present invention is provided. As shown therein, one or more cationic conditioning agents are also preferably incorporated into the preferred formulation, along with methyl ethyl alcohol and/or ammonium hydroxide, and enhancing additives. Preferably, the enhancing additives comprise one or more selected from the group consisting of fatty alcohols, fattening agents, emulsifiers, and perfumes.

TABLE I

Hair Dye/Hair Coloring Composition

| Ingredient | Range % by Weight |
| --- | --- |
| Polyquaternium-53 | 0.1–5 |
| Dyes, dye carriers, solvents and anti-oxidants | 7–15 |
| Linoleamidopropyl Dimethylamine Dimer Dilinoleate | 0–5 |
| Behentrimonium Methosulfate | 0–8 |
| Amodimethicone | 0–5 |
| Additives | 15–25 |
| MEA and Ammonium Hydroxide (28%) | 8–15 |
| Water | q.s. to 100% |

In Table II, detailed formulations are provided for two alternate compositions which employ the teaching of the present invention and have been found to provide the desired enhanced results.

TABLE II

Preferred Hair Dye/Hair Coloring Formulations

| Ingredient | Formulation A % by Weight | Formulation B % by Weight |
| --- | --- | --- |
| Polyquaternium-53 | 2 | 2 |
| Dyes, and anti-oxidants | 1 | 1 |
| Solvents and dye carriers | 11 | 11 |
| Linoleamidopropyl Dimethylamine Dimer Dilinoleate | 3 | — |
| Behentrimonium Methosulfate | 5 | 5 |
| Amodimethicone | 3 | — |
| MEA and Ammonium Hydroxide (28%) | 12 | 12 |
| Fatty alcohols, fattening agents and emulsifiers | 21 | 21 |
| Perfume | 0.8 | 0.8 |
| Water | 41.2 | 47.2 |

BEST MODE FOR CARRYING OUT THE INVENTION

In order to demonstrate the efficacy of the present invention and the achievement of a hair dye or hair coloring composition which provides long lasting hair coloring, while also achieving substantially enhanced conditioning of the hair fibers, a plurality of alternate compositions were manufactured in accordance with the present invention and tested as detailed below. The following examples are presented in order to fully demonstrate the highly effective hair dye and hair coloring compositions of the present invention and the substantially enhanced results achieved thereby.

By reviewing the following examples, the ability of the hair dye or hair coloring compositions of the present invention to provide the desired results is clearly established. However, it is to be understood that the following examples are intended as a teaching of the best mode for carrying out the present invention and are not intended to limit the breadth of this discovery.

In providing these comparative examples and analysis, it is important to realize that many different techniques have been developed and are accepted in the cosmetic industry for determining the existence and extent of conditioning benefits delivered to hair fibers from a hair treatment. One such well-accepted test standard is the Rubine Dye test which is effectively employed for measuring the presence of a cationic compound on hair fibers. Since the present invention employs a quaternary polymer which dramatically contributes to conditioning benefits by depositing a cationic moiety to the hair surface, it has been found that the Rubine Dye test is most effective for demonstrating the efficacy of the present invention. As detailed below, the conditioning benefits provided by the present invention were evaluated for hair fibers that were colored and then shampooed 3, 7, 14, and up to 20 times.

Furthermore, the Rubine dye test is a quick and selective test that can be performed to identify cationic moiety on the hair as well as establish how long this cationic moiety will remain on the hair through washings. The anionic Rubine dye (direct red 80) complexes with cationic materials deposited on the hair by the test product. The hair is then rinsed with tap water and visually evaluated for the presence of a pink color. The intensity of the color (pink to purple) is an indication of the presence and the relative amount of the quaternary polymer that is bound to the hair. Throughout these test procedures, colorless albino human hair was employed, which was purchased from International Hair Importers.

EXPERIMENT 1

Comparative Evaluation of Cationic Conditioning Benefits of Hair Color Brands via Rubine Dye Test When we first noticed the highly conditioning properties of the claimed composition, it seemed relevant to compare the composition of this invention to the currently marketed hair coloring products. We selected four currently marketed hair color brands: Socolor by Matrix; Kolestone Perfect by Wella; Topchic by Goldwell; and Daniel Galvin by ISO.

Nineteen tresses of Piedmont hair, approximately 1 g each in weight, were prepared by washing in ethanol followed by deionized water twice and dried. Three tresses were not dyed and were used as baseline color controls for our method as follows: one tress remained untouched; the second tress was not dyed, but was soaked in the Rubine dye solution; the third tress was shaken in a 15% SLS solution for 15 minutes and then soaked in the Rubine dye solution.

Four tresses were treated with each of the four test products: Socolor, 9G; Kolestone Perfect 10/0; Topchic 9NA; and Daniel Galvin, 100N. Each color was mixed with the recommended developer and applied according to the manufacturer's procedure. After processing, the test swatches were thoroughly washed with water until the water ran clean. An additional tress was treated with Formula A (Table II) in accordance with the present invention.

One tress of each product was set aside, and the other three were placed in separate jars filled with 100 ml of a 15% SLS solution. The jars were placed in a heated sonicator and left vibrating to simulate washing in hot water. One tress of each product was taken out after 15 minutes, the second was taken out after 30 minutes, and the last one was finally removed after 45 minutes. All tresses, including the one that was not washed, were immersed in 0.1% Rubin Dye solution for one minute, removed and rinsed with running tap water for 2 minutes. It should be noted that each of the tresses was immersed in the solution using a separate beaker to avoid cross-contamination.

First, we evaluated the results of the baseline control tresses. The tress left untouched was slightly yellow piedmont hair. The second tress that was not dyed with any hair color, just soaked in Rubin dye solution, remained colorless as well. The third tress that was shaken in warm SLS solution for 15 minutes and then soaked in the Rubin dye solution, had some faint pink color on the top of the tress fading down to colorless on the bottom.

The results observed for the four existing products and our test composition are summarized in Table III. The color of the test swatch indicates a cationic deposition on the hair. The substantivity of this cationic deposition is indicated by the pink color still showing on the hair tress that was shaken in 15% SLS solution for 15 minutes, 30 minutes, and 45 minutes.

The hair coloring composition of the present invention contains Polyquaternium-53 in addition to other cationic materials. This composition leaves a strong cationic charge on the hair as shown by the pink color on the hair after being soaked in the Rubine dye solution. These tests show that Polyquaternium-53 bounds itself to the hair in greater amount. This substantivity also remains strong after the hair is shampooed numerous times. We have tested various cationic materials present in the hair color compositions alone and in combination with each other to determine which cationic material delivers long-lasting conditioning.

Our hair coloring compositions were mixed with developed and applied to the hair swatches in the same manner. The hair was then washed to completely remove the product and allowed to dry.

TABLE III

Results of Rubin Dye Test for Hair Coloring Compositions

| | Rubine Dye Test Results | | | |
|---|---|---|---|---|
| Test Product | After Coloring | 15 Min. shaking in SLS | 30 Min. shaking in SLS | 45 Min. shaking in SLS |
| Wella Kolestone Perfect Shade 10N | Very faint pink | baseline | baseline | baseline |
| Goldwell, Shade 9NA | Very faint pink | baseline | baseline | baseline |
| Matrix Socolor, Shade 9G | Very faint pink | baseline | baseline | baseline |
| Daniel Galvin, Shade 100N | Very faint pink | baseline | baseline | baseline |
| Formula A from Table II | Pink | Pink | Pink | Pink |

During this testing, we discovered that the tested commercial hair color products deposit very little cationinc moiety on the surface, and it can be quickly removed by the SLS solution. However, our claimed composition behaved quite differently, by depositing a cationic moiety on the hair that remained substantive after thorough stripping in an anionic SLS solution.

EXPERIMENT II

Evaluation of Conditioning Properties of Cationic Condition Agents

The hair coloring composition encompassed by this invention may contain various cationic materials, such as quaternized guar gum, amino-functional silicone or quaternary ammonium compounds. As we have learned, all of them deposit a very small cationic charge on the hair during the dyeing process.

As shown in Table IV, Formulas A and B, as defined in Table II, were tested and compared to Composition C which contained three cationic conditioning agents, Linoleamidopropyl Dimethylamine Dimer Dilinoleate, Behentrimonium Methosulfate, and Amodimethicone. However, the composition did not contain Polyquaternium-53. In addition, all three compositions were prepared with Behenyltrimoniium Methosulfate (and) Cetearyl Alcohol (Incroquat Behenyl TMS by Croda) which was employed to form a cream.

As shown in Table IV, at the bottom of the table, Composition C produced a very faint pink color due to the effect of the three cationic conditioners. This color is comparable to the baseline controls seen with the other competitive hair color products. However, by adding 2% Polyquaternium-53, the color achieved by the Rubine dye test changed to deep pink.

TABLE IV

Substantivity of Various Cationic Materials in Hair Coloring Compositions

| Components | Formula A Weight Percent | Formula B Weight Percent | Composition C Weight Percent |
|---|---|---|---|
| Water | 41.2 | 47.2 | 43.2 |
| Fatty alcohols, fattening agents and emulsifiers | 21 | 21 | 21 |
| Solvents and dye carriers | 11 | 11 | 11 |
| Dyes and anti-oxidants | 1 | 1 | 1 |
| Linoleamidopropyl Dimethylamine Dimer Dilinoleate (cationic) | 3 | — | 3 |
| Behentrimonium Methosulfate | 5 | 5 | 5 |
| Amodimethicone (cationic) | 3 | — | 3 |
| Polyquaternium-53 | 2 | 2 | — |

TABLE IV-continued

Substantivity of Various Cationic Materials in Hair Coloring Compositions

| Components | Formula A Weight Percent | Formula B Weight Percent | Composition C Weight Percent |
|---|---|---|---|
| Perfume | 0.8 | 0.8 | 0.8 |
| MEA and Ammonium Hydroxide (28%) | 12 | 12 | 12 |
| Rubine Test Results | Deep Pink | Deep Pink | Very Faint Pink |

EXPERIMENT III

We have evaluated the longevity of the cationic deposition achieved from Formula A of the present invention on the hair via manual shampoo washings using industry recommended Rubine Dye Test.

Rubine Dye Solution: 1% direct Red 80 was prepared as follows:
10 g Direct Red 80
Approximately 2.5 g of Glacial Acetic acid
Deionized Water, qs to 100 ml
pH=3.50 (adjusted with MEA if necessary)

A strip of piedmont hair, 10" wide, was washed with ethanol, then rinsed twice with deionized water and dried. The hair was dyed with the Formula A. The hair looked very light pale blonde. The strip was then cut into 1" swatches. Each swatch was manually shampooed using a simplified shampoo solution made with 7% ammonium lauryl sulfate and 4% cocoamidopropyl betaine. The swatches were gently rubbed for 1 minute with 1 g of shampoo solution, then rinsed for 30 seconds in tap water. The four test swatches were shampooed 3 times, 7 times, 14 times and 20 times, respectively. Afterwards, the swatches were soaked in Rubine dye solution for 1 minute and rinsed under running tap water for 2 minutes. The swatches were dried and evaluated. The control swatch was not dyed, only soaked in Rubine dye solution. Resulting swatches show that the control swatch has no color. The swatches that were colored are described in Table V below.

TABLE V

| Test Swatches | Control | 0 Washes | 3 Washes | 7 Washes | 14 Washes | 20 Washes |
|---|---|---|---|---|---|---|
| Test Results | No color | Vivid pink | Light pink | Light pink | Light pink | Faint pink |

It will thus be seen that the objects set forth above, among those made apparent from the preceding description, are efficiently attained and that, since certain changes may be made in the above compositions and methods without departing from the scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

Having described our invention, what we claim as new and desired to secure by Letters Patent is:

1. A hair dye or hair coloring composition comprising a mixture of:
   A. at least one dye selected from the group consisting of oxidative dyes and direct dyes; and
   B. a quaternary amphoteric terpolymer comprising repeating units of the following moieties
      a. methacrylamidopropyl trimethyl ammonium chloride (MAPTAC),
      b. one selected from the group consisting of acrylic acid and sodium methacrylate,
      c. acrylamide, and
      d. the ratio of moiety (a) to the moiety (b) being 4:1 or higher.

2. The hair dye/hair coloring composition defined in claim 1, wherein the acrylic acid is further defined as being partly or completely neutralized into a cationic polymer.

3. The hair dye/hair coloring composition defined in claim 1, wherein the amphoteric terpolymer is further defined as comprising a reaction product consisting of about 25 mole percent of one selected from the group consisting of acrylic acid and sodium acrylate, about 50 mole percent of methylamidopropyl trimethyl ammonium chloride, and about 25 mole percent of acrylamide.

4. The hair dye/hair coloring composition defined in claim 1, wherein said composition is further defined as comprising between about 0% and 5% by weight based upon the weight of the entire composition of the dye, and between about 0% and 5% by weight based on the weight of the entire composition of the amphoteric terpolymer.

5. The hair dye/hair coloring composition defined in claim 1, wherein said composition is further defined as comprising a pH ranging between about 8 and 11.

6. The hair dye/hair coloring composition defined in claim 1, wherein said dye is further defined as comprising at least one dye selected from the group consisting of p-phenylenediamine, p-tolyenediamine, and its derivatives, N,N-Bis(2-hydroxyethyl)-p-phenylenediamine, p-aminophenol, 2-chloro-p-phenylenediamine, 2-methoxy-p-phenylenediamine, resorcinol, 1-naphthol, 2-amino-3-hydroxytoluene, m-aminophenol, p-amino-o-cresol, 2-methyl-resorcinol, m-phenylenediamine and mixtures thereof.

7. The hair dye/hair coloring composition defined in claim 1, wherein said composition is further defined as being intermixed with a developer containing at least one oxidizing agent selected from the group consisting of peroxide, perborate, and percarbonate.

8. A hair dye or hair coloring composition comprising a mixture of:
- A. between about 7% and 15% by weight based upon the weight of the entire composition of at least one dye selected from the group consisting of oxidative dyes and direct dyes, dye carriers, solvents, and anti-oxidants;
- B. between about 0.5% and 5% by weight based upon the weight of the entire composition consisting of a quaternary amphoteric terpolymer comprising repeating units of the following moieties
  1. methacrylamidopropyl trimethyl ammonium chloride (MAPTAC),
  2. one selected from the group consisting of acrylic acid and sodium methacrylate,
  3. acrylamide, and
  4. the ratio of moiety (a) to the moiety (b) being 4:1 or higher
- C. between about 0% and 5% by weight based upon the weight of the entire composition of linoleamidopropyl dimethylamine dimer dilinoleate;
- D. between about 0% and 8% by weight based upon the weight of the entire composition of behentrimonium methosulfate;
- E. between about 0% and 5% by weight based upon the weight of the entire composition of amodimethicone;
- F. between about 15% and 25% by weight based upon the weight of the entire composition of additives;
- G. between about 8% and 15% by weight based upon the weight of the entire composition of at least one ingredient selected from the group consisting of methyl ethyl alcohol and ammonium hydroxide; and
- H. water forming the balance.

9. A hair dye or hair coloring composition comprising a mixture of:
- A. about 2% by weight based upon the weight of the entire composition of polyquaternium-53;
- B. about 1% by weight based upon the weight of the entire composition of dyes and anti-oxidants;
- C. about 11% by weight based upon the weight of the entire composition of solvents and dye carriers;
- D. about 3% by weight based upon the weight of the entire composition of linoleamidopropyl dimethylamine dimer dilinoleate;
- E. about 5% by weight based upon the weight of the entire composition of amodimethicone;
- F. about 12% by weight based upon the weight of the entire composition of methyl ethyl alcohol and ammonium hydroxide;
- G. about 21% by weight based upon the weight of the entire composition of fatty alcohols, fattening agents and emulsifiers;
- H. about 0.8% by weight based upon the weight of the entire composition of perfume; and
- I. water forming the balance.

* * * * *